US00RE36433E

United States Patent [19]

Villa et al.

[11] E Patent Number: Re. 36,433

[45] Reissued Date of Patent: Dec. 7, 1999

[54] PROCESS FOR THE PURIFYING OF IOPAMIDOL

[75] Inventors: Marco Villa; Maurizio Paiocchi, both of Milan, Italy

[73] Assignee: Bracco International B.V., Amsterdam, Netherlands

[21] Appl. No.: 08/797,610

[22] Filed: Feb. 7, 1997

Related U.S. Patent Documents

Reissue of:

[64] Patent No.: 5,571,941
Issued: Nov. 5, 1996
Appl. No.: 08/281,985
Filed: Jul. 29, 1994

[30] Foreign Application Priority Data

Jul. 30, 1993 [IT] Italy ..... MI93A1720
Apr. 20, 1994 [IT] Italy ..... MI94A0760

[51] Int. Cl.[6] ..... C07C 231/22

[52] U.S. Cl. ..... 564/153; 564/152; 424/9.454

[58] Field of Search ..... 424/9.454; 564/152, 564/153

[56] References Cited

U.S. PATENT DOCUMENTS 4,001,323 1/1977 Felder et al. .
4,352,788 10/1982 Felder et al. .
5,066,823 11/1991 Felder et al. .
5,204,086 4/1993 Wille .

FOREIGN PATENT DOCUMENTS 1472050 4/1977 United Kingdom .
WO92/14539 9/1992 WIPO .

OTHER PUBLICATIONS

Analytical Profiles of Drug Substances, vol. 17, pp. 115–154, Academic Press, San Diego, 1988 (cited in parent).

U.S. Pharmacopeia xxii, p. 712, 1990 (cited in parent).

Boll. Chim. Farm., 120, 639 (1981), (cited in parent).

Merck Index 10$^{th}$Edition, 4915, p. 731, 1983 (cited in parent).

*Primary Examiner*—Shailendra Kumar
*Attorney, Agent, or Firm*—Oblon, Spivak, McClelland, Maier & Neustadt, P.C.

[57] ABSTRACT

A process for purifying Iopamidol which uses a butanol as solvent is described. Iopamidol is obtained with high yields, also starting from aqueous solutions of the same and has characteristics in accordance with those required by pharmacopoeia.

14 Claims, No Drawings

PROCESS FOR THE PURIFYING OF IOPAMIDOL

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a process for purifying Iopamidol and, more particularly, to a process for purifying Iopamidol using butanol as solvent.

2. Discussion of the Background

Iopamidol is the International non-proprietary Name (INN) for L-5-α-hydroxypropionylamino-2,4,6-triiodoisophthalic acid bis-(1,3-dihydroxyisopropylamide). This compound was first described by the Swiss company Savac A.G. in the British patent no. 1,472,050. Iopamidol is used in diagnostics as non-ionic contrast medium.

Iopamidol is a white high-melting solid. Conventional syntheses of Iopamidol involve a final purification of the product in an aqueous solution. Thereafter, in order to obtain the product in solid form, it is necessary to crystallize it.

British patent No. 1,472,050 describes that Iopamidol can be isolated by evaporation of the aqueous solution followed by crystallization of the crude product obtained from ethanol. WO 88/09328 to Bracco Industria Chimica S.p.A. describes that crude Iopamidol can be obtained by evaporation of the aqueous solution followed by crystallization of the crude product from absolute ethanol. "Analytical Profiles of Drug Substances", vol. 17, pages 115–154, Academic Press, San Diego, 1988) describes that Iopamidol can be crystallized from water, with very slow kinetics, yielding a monohydrate or pentahydrate crystalline product.

Unfortunately when Iopamidol is crystallized from water or ethanol as described in the literature, a crystalline form having the required pharmaceutical properties as described in US Pharmacopoeia XXII, page 712, cannot be obtained. The product crystallized from ethanol contains an amount of ethanol corresponding to 4000–8000 ppm which cannot be removed either by heating at high temperatures or under vacuum. This product is not suitable as a pharmaceutical because its ethanol content is too high (the USA Pharmacopoeia requires that no impurity can exceed 5000 ppm). Similarly, Iopamidol crystallized from water is not suitable because in order to remove the water of crystallization, very long heating times at temperatures higher than 100° C. are required. Furthermore, the yield of the crystallization from water is very poor and therefore the process is not suitable from an industrial point of view.

The literature data regarding the solubility of Iopamidol conflict with each other and therefore they do not suggest other practical solutions to solve these problems. For example, British patent no. 1,472,050 reports that Iopamidol dissolves very easily in water, has a practically unlimited solubility in methanol and has solubility in ethanol of about 10% at room temperature. However, one of the inventors of that patent, in a subsequent paper published on Boll. Chim. Farm., 120, 639, (1981), reports that Iopamidol is very soluble in water but is only slightly soluble in methanol and practically insoluble in ethanol, diethylether, benzene and chloroform. Accordingly, it is desirable to find a practical and efficient method for purifying Iopamidol.

SUMMARY OF THE INVENTION

Accordingly, it is one object of the present invention to provide a method for purifying Iopamidol from a crude solid form of Iopamidol.

It is a second object of the present invention to provide a process for purifying Iopamidol from an aqueous solution of Iopamidol.

It is a third object of the present invention to provide essentially pure Iopamidol.

The present inventors have now surprisingly found that these and other objects can be achieved by crystallizing Iopamidol from n-butanol, sec-butanol, isobutanol or t-butanol. The present inventors have further found that it is not necessary to start from solid crude Iopamidol but it is possible to obtain the desired product by directly treating an aqueous solution of Iopamidol with n-butanol, sec-butanol, isobutanol or t-butanol.

DETAILED DESCRIPTION OF THE PREFERRED EMBODIMENTS

The terms n-butanol, sec-butanol, isobutanol and t-butanol are the common names used to indicate the four isomers of butanol having the formula $C_4H_{10}O$; more precisely, n-butanol is the common name for 1-hydroxybutane, sec-butanol is the common name for 2-hydroxybutane, isobutanol is the common name for 1-hydroxy-2-methylpropane and t.butanol is the common name for 1,1-dimethyl-1-hydroxyethane. Hereinafter, for the sake of simplicity, the term butanol is used to indicate indifferently n-butanol, sec-butanol, isobutanol or t-butanol, if not otherwise specified.

Iopamidol can be synthesized using known techniques such as those described in U.S. Pat. No. 4,001,323; incorporated herein by reference. Crude Iopamidol can be isolated as described in British patent no. 1,427,050; WO 88/09328 and "Analytical Profiles of Drug Substances, vol. 17, pages 115–154, Academic Press. San Diego; each of which is incorporated herein by reference. Preferably, Iopamidol is isolated by distillation until crude Iopamidol begins to crystallize.

Thereafter pharmaceutically pure Iopamidol is isolated by crystallizing crude Iopamidol from butanol. In a first embodiment solid crude Iopamidol is crystallized from butanol. In a second embodiment, an aqueous solution of crude Iopamidol is crystallized by adding butanol to form a crystallization mixture. The amount of residual water in the crystallization mixture, for example even an amount of water equal to the weight of Iopamidol, does not effect either the quality or the yield of pure Iopamidol.

The amount of butanol to be used is from 3 to 20 times (volume/weight) with respect to the amount of Iopamidol which is present in the aqueous solution. Preferably, the amount of butanol is from 3 to 12 times (volume/weight) with respect to the amount of Iopamidol. Still more preferably, the amount of butanol is from 3 to 10 times (volume/weight) with respect to the amount of Iopamidol. It is self-evident that when there is an azeotropic mixture, butanol can be recovered by distillization and recycled.

In a third embodiment of the present invention, a third solvent can also be added to the crystallization mixture of water, Iopamidol and butanol. The third solvent suitably is able to form a ternary azeotrope with water. A preferred third solvent is toluene.

From a practical point of view, the direct use of an aqueous solution of Iopamidol is preferred because it is practically and economically more advantageous not to remove all the water and because the resultant product has a very low content of residual solvent. It is particularly advantageous from an industrial point of view to purify Iopamidol from an aqueous solution of Iopamidol and butanol in an amount from 3 to 20 times (volume/weight) with respect to that of Iopamidol. The reaction mixture is heated at the boiling temperature to azeotropically remove part of the water. Precipitation of Iopamidol is observed. The distillation is continued until the water is reduced to an weight amount equal to or lower than that of Iopamidol. Then, the heating is stopped and the temperature is brought to 10°–30° C., preferably to about 25° C., and Iopamidol is separated by filtration.

Alternatively, the crystallization mixture of water. Iopamidol and butanol is added with a third solvent able to from an azeotrope with water, for example toluene. As above, during the distillation step a precipitate of Iopamidol begins to form.

Iopamidol obtained by the process of the present invention is pharmaceutically acceptable since the amount of butanol remaining in the product is decidedly lower than the required limits. As used herein, pure Iopamidol contains an amount of residual solvent which is less than the amount of residual solvent in the crude Iopamidol used as the starting material. Preferably, the pure Iopamidol obtained has at most 2000 ppm of residual solvent. In fact, when Iopamidol is obtained directly from the aqueous solution, the residual solvent is even equal to or lower than 200 ppm. The resultant product has a very high chromatographic purity, higher than that of the starting product in aqueous phase. Thus, the Iopamidol obtained by the purification process of the invention is particularly suitable for the preparation of nonionic contrast media according to usual techniques.

Furthermore, the crystallization yields are very high, at least higher than 80% and in most cases also higher than 95%.

As far as the instant process is concerned, mixtures of butanols appear to behave in substantially the same way as the single components and thus mixture of butanols do not depart from the spirit of this invention.

Having generally described this invention, a further understanding can be obtained by reference to certain specific examples which are provided herein for purposes of illustration only and are not intended to be limiting unless otherwise specified.

EXAMPLES

The water content in the azeotrope and in the final product was determined by Karl-Fisher method, while the content of butanol in the final product was determined by gas-chromatographic route.

Example 1

Sec-butanol (1600 ml) was added under stirring and by keeping the temperature at 85° C. to a solution of Iopamidol (200 g; 0.257 moles) in water (200 ml). The solution was heated to the reflux temperature, while distilling at ordinary pressure the mixture sec-butanol/water at the rate of 10 mil/minute. During the distillation Iopamidol begins to precipitate. In all, 853 g of sec-butanol/water mixture (water=23.1%) were distilled off. The suspension was cooled to 25° C. in 1 hour, kept at 25° C. for one further hour and the precipitate was filtered off and washed with sec-butanol (2×100 ml). After drying under vacuum at 60° C. until constant weight, Iopamidol (192 g; 0.247 moles; 96% yield) was obtained; water content=0.15% and residual solvent sec-butanol 200 ppm.

Example 2

Sec-butanol (1800 ml) was added under stirring and by keeping the temperature at 80° C.±2° C. to a solution of Iopamidol (200 g, 0.257 moles) in water (270 ml). The solution was heated to the reflux temperature, while distilling at ordinary pressure the mixture sec.butanol/water at the rate of 10 ml/minute. During the distillation Iopamidol begins to precipitate. In all, 700 g of sec-butanol/water mixture (water=22%) were distilled off. About 116 g of water were still present. The suspension was cooled to 25° C. in 1 hour, kept at 25° C. for one further hour and the precipitate was filtered off and washed with sec-butanol (2×100 ml). After drying under vacuum at 60° C. until constant weight, Iopamidol (190 g; 0.244 moles; 95% yield) was obtained; water content=0.2%, residual solvent sec-butanol 180 ppm.

Example 3

Sec-butanol (150 ml) and toluene (20 ml) were added under stirring and by keeping the temperature at 80°–85° C. to a solution of Iopamidol (20 g; 0.0257 moles) in water (30 ml). The mixture was brought to reflux and a part of water was azeotropically removed. During the distillation Iopamidol begins to precipitate. In all, 12 ml of water were distilled off. The suspension was cooled in 1 hour to 25° C., kept at 25° C. for one further hour and the precipitate was filtered off and washed with sec-butanol (2×10 ml). After drying under vacuum at 60° C. until constant weight, Iopamidol 19.2 g; 0.0247 moles; 96% yield) was obtained; water content=0.2%, residual solvent sec-butanol 100 ppm and toluene 2 ppm.

Example 4

N-butanol (200 ml) was added under stirring and by keeping the temperature at 80° C.±2° C. to a solution of Iopamidol (20 g; 0.0257 moles) in water (20 ml). The solution was heated to the reflux temperature, while distilling water (8.5 g) with a florentine flask. During the distillation Iopamidol begins to precipitate. The distillation was completed by further distilling 54 g of n-butanol/water mixture (water=21%). The suspension was cooled to 25° C. and the precipitate was filtered off and washed with n-butanol (2×10 ml). After drying under vacuum at 60° C. until constant weight. Iopamidol 19.4 g; 0.025 moles; 97% yield) was obtained; water content=0.2%, residual solvent n-butanol 70 ppm.

Example 5

N-butanol (200 ml) was added under stirring and by keeping the temperature at 80° C.±2° C. to a solution of Iopamidol (20 g; 0.0257 moles) in water (80 ml). The solution was heated to boiling, while distilling water (72 g) with a florentine flask. During the distillation Iopamidol begins to precipitate. The distillation was completed by further distilling 50 g of n-butanol/water mixture (water=21%). The suspension was cooled to 25° C. and the precipitate was filtered off and washed with n-butanol (2×10 ml). After drying under vacuum at 60° C. until constant weight, Iopamidol (19.3 g; 0.0248 moles; 96.5% yield) was obtained; water content=0.2%, residual solvent n-butanol 80 ppm.

Example 6

A solution of Iopamidol (20 g; 0.0257 moles) in water (20 ml) was brought to residue under vacuum (70° C.–30 mmHg). Sec-butanol (150 ml) was added to the residue containing water (2.3%) and the heterogeneous mixture, kept under stirring, was brought to reflux and kept at the reflux temperature for 30 minutes. The suspension was cooled to 25° C. and the precipitate was filtered off and washed with sec-butanol (2×10 ml). After drying under vacuum at 70° C. until constant weight, Iopamidol (19.4 g; 0.025 moles; 97% yield) was obtained; water content=0.2%, residual solvent n-butanol 1300 ppm.

Example 7

A mixture of Iopamidol (20 g; 0.0257 moles), water (20 ml) and isobutanol (150 ml) was heated to reflux while distilling water (9 ml).

During the distillation Iopamidol begins to precipitate. In all, 47 g of isobutanol/water mixture (water=18.3%) were distilled off. The suspension was cooled to 25° C. and the precipitate was filtered off and washed with isobutanol (2×10 ml).

After drying under vacuum at 60° C. until constant weight, Iopamidol (19.7 g; 0.0254 moles; 98.5% yield) was obtained; water content=0.17%, residual solvent isobutanol 100 ppm.

Example 8

T-butanol (150 ml) was added under stirring and by keeping the temperature at 70° C. to a solution of Iopamidol (20 g; 0.0257 moles) in water (20 ml). The suspension was heated to the reflux temperature, while distilling at ordinary pressure 57 g of the mixture t-butanol/water (water=13.3%). During the distillation Iopamidol begins to precipitate. The suspension was cooled to 25° C. and the precipitate was filtered off and washed with t-butanol (2×10 ml). After drying under vacuum at 60° C. until constant weight, Iopamidol (16 g; 0.0206 moles; 80% yield) was obtained; water content=0.25%, residual solvent t-butanol 150 ppm.

Example 9

Charcoal (8 Kg) was added to an aqueous solution (2500 l) containing Iopamidol (about 290 Kg). After stirring for 30 minutes and filtration of the charcoal, the resultant solution was concentrated under vacuum up to a final concentration of 70–75% (w/w). The concentrated solution was heated to 85° C. and, while keeping the temperature between 80° C. and 85° C., sec.butanol (1300 Kg) was added. At the end of the addition, the resultant suspension was kept at 80°–85° C. for 30 minutes and then cooled to 25° C. After stirring at 25° C. for 2 hours and filtration, the solid residue was washed with sec-butanol (190 Kg) and dried at 50°–55° C. under vacuum. Pure Iopamidol (275 Kg) was obtained.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for purifying L-5-α-hydroxypropionylamino-2,4,6-triiodo-isophthalic acid bis-(1,3-dihydroxyisopropylamide) (Iopamidol) comprising the steps of:

dissolving a crude solid of Iopamidol in sec-butanol; and crystallizing pure Iopamidol therefrom, wherein said pure Iopamidol has less residual solvent than said crude Iopamidol.

2. The process of claim 1, wherein the weight of Iopamidol to the volume of solvent is 3 to 20.

3. A process for purifying L-5-α-hydroxypropionylamino-2,4,6-triiodo-isophthalic acid bis-(1,3-dihydroxyisopropylamide) (Iopamidol) comprising the steps of:

treating an aqueous solution of Iopamidol with sec-butanol, to obtain a mixture containing Iopamidol; and

[crystallizing pure Iopamidol therefrom, dissolving a crude solid of Iopamidol in sec-butanol; and]

crystallizing pure Iopamidol therefrom, wherein said pure Iopamidol has less residual solvent than said crude Iopamidol.

4. The process of claim 3, wherein said aqueous solution of Iopamidol is the product of a synthesis of Iopamidol.

*5. A process for purifying L-5-α-hydroxypropionylamino-2,4,6-triiodo-isophthalic acid bis-(1,3-dihydroxyisopropylamide), comprising the steps of:*

*treating a crude solid of L-5-α-hydroxypropionylamino-2,4,6-triiodo-isophthalic acid bis-(1,3-dihydroxyisopropylamide) with sec-butanol; and*

*crystallizing L-5-α-hydroxypropionylamino-2,4,6-triiodo-isophthalic acid bis-(1,3-dihydroxyisopropylamide) therefrom.*

*6. The process of claim 5, wherein said L-5-α-hydroxypropionylamino-2,4,6-triiodo-isophthalic acid bis-(1,3-dihydroxyisopropylamide) is treated with a volume as measured in ml of sec-butanol which is 3 to 20 times the weight as measured in grams of L-5-α-hydroxypropionylamino-2,4,6-triiodo-isophthalic acid bis-(1,3-dihydroxyisopropylamide).*

*7. A process for purifying L-5-α-hydroxypropionylamino-2,4,6-triiodo-isophthalic acid bis-(1,3-dihydroxyisopropylamide), comprising the steps of:*

*(i) adding sec-butanol to an aqueous solution of L-5-α-hydroxypropionylamino-2,4,6-triiodo-isophthalic acid bis-(1,3-dihydroxyisopropylamide) to obtain a suspension comprising L-5-α-hydroxypropionylamino-2,4,6-triiodo-isophthalic acid bis-(1,3-dihydroxyisopropylamide), water, and sec-butanol; and*

*(ii) crystallizing L-5-α-hydroxypropionylamino-2,4,6-triiodo-isophthalic acid bis-(1,3-dihydroxyisopropylamide) from said suspension comprising L-5-α-hydroxypropionylamino-2,4,6-triiodo-isophthalic acid bis-(1,3-dihydroxyisopropylamide), water and sec-butanol.*

*8. The process of claim 7, wherein said aqueous solution of L-5-α-hydroxypropionylamino-2,4,6-triiodo-isophthalic acid bis-(1,3-dihydroxyisopropylamide) has been contacted with charcoal and filtered to remove said charcoal prior to said adding sec-butanol.*

*9. The process of claim 7, wherein said sec-butanol is added to said aqueous solution of L-5-α-hydroxypropionylamino-2,4,6-triiodo-isophthalic acid bis-(1,3-dihydroxyisopropylamide) in a volume as measured in ml which is 3 to 20 times the weight as measured in grams of L-5-α-hydroxypropionylamino-2,4,6-triiodo-isophthalic acid bis-(1,3-dihydroxyisopropylamide) in said aqueous solution of L-5-α-hydroxypropionylamino-2,4,6-triiodo-isophthalic acid bis-(1,3-dihydroxyisopropylamide).*

*10. The process of claim 7, wherein said sec-butanol is added to said aqueous solution of L-5-α-hydroxypropionylamino-2,4,6-triiodo-isophthalic acid bis-(1,3-dihydroxyisopropylamide) in a volume as measured in ml which is 3 to 12 times the weight as measured in grams of L-5-α-hydroxypropionylamino-2,4,6-triiodo-isophthalic acid bis-(1,3-dihydroxyisopropylamide) in said aqueous solution of L-5-α-hydroxypropionylamino-2,4,6-triiodo-isophthalic acid bis-(1,3 dihydroxyisopropylamide).*

*11. The process of claim 7, wherein said sec-butanol is added to said aqueous solution of L-5-α-hydroxypropionylamino-2,4,6-triiodo-isophthalic acid bis-*

(1,3-dihydroxyisopropylamide) in a volume as measured in ml which is 3 to 10 times the weight as measured in grams of L-5-α-hydroxypropionylamino-2,4,6-triiodo-isophthalic acid bis-(1,3-dihydroxyisopropylamide) in said aqueous solution of L-5-α-hydroxypropionylamino-2,4,6-triiodo-isophthalic acid bis-(1,3-dihydroxyisopropylamide).

12. The process of claim 7, wherein said aqueous solution of L-5-α-hydroxypropionylamino-2,4,6-triiodo-isophthalic acid bis-(1,3-dihydroxyisopropylamide) is concentrated to a concentration of 70 to 75% (w/w) prior to said adding sec-butanol.

13. The process of claim 7, wherein said aqueous solution of L-5-α-hydroxypropionylamino-2,4,6-triiodo-isophthalic acid bis-(1,3-dihydroxyisopropylamide) is maintained at a temperature between 80 and 85° C. during said adding sec-butanol.

14. A process for purifying L-5-a-hydroxypropionylamino-2,4,6-triiodo-isophthalic acid bis-(1,3-dihydroxyisopropylamide), comprising the steps of:

(i) adding charcoal to a first aqueous solution of L-5-α-hydroxypropionylamino-2,4,6-triiodo-isophthalic acid bis-(1,3-dihydroxyisopropylamide) to obtain a mixture;

(ii) filtering said mixture to obtain a second aqueous solution of L-5-a-hydroxypropionylamino-2,4,6-triiodo-isophthalic acid bis-(1,3-dihydroxyisopropylamide);

(iii) concentrating said second aqueous solution of L-5-α-hydroxypropionylamino-2,4,6-triiodo-isophthalic acid bis-(1,3-dihydroxyisopropylamide) to a concentration of 70% to 75% (w/w), to obtain a third aqueous solution of L-5-α-hydroxypropionylamino-2,4,6-triiodo-isophthalic acid bis-(1,3-dihydroxyisopropylamide);

(iv) heating said third aqueous solution of L-5-α-hydroxypropionylamino-2,4,6-triiodo-isophthalic acid bis-(1,3-dihydroxyisopropylamide);

(v) adding sec-butanol to said heated aqueous solution of L-5-α-hydroxypropionylamino-2,4,6-triiodo-isophthalic acid bis-(1,3-dihydroxyisopropylamide), to obtain a suspension comprising L-5-α-hydroxypropionylamino-2,4,6-triiodo-isophthalic acid bis-(1,3-dihydroxyisopropylamide), water, and sec-butanol;

(vi) maintaining said suspension comprising L-5-α-hydroxypropionylamino-2,4,6-triiodo-isophthalic acid bis-(1,3-dihydroxyisopropylamide), water and sec-butanol at a temperature of 80 to 85° C. for a time of about 30 minutes and then cooling said suspension comprising L-5-α-hydroxypropionylamino-2,4,6-triiodo-isophthalic acid bis-(1,3-dihydroxyisopropylamide), water, and sec-butanol, to obtain a cooled suspension;

(vii) stirring said cooled suspension for about 2 hours and then filtering said cooled solution to obtain solid L-5-α-hydroxypropionylamino-2,4,6-triiodo-isophthalic acid bis-(1,3-dihydroxyisopropylamide);

(viii) washing said solid L-5-α-hydroxypropionylamino-2,4,6-triiodo-isophthalic acid bis-(1,3-dihydroxyisopropylamide) with sec-butanol, to obtain washed solid L-5-α-hydroxypropionylamino-2,4,6-triiodo-isophthalic acid bis-(1,3-dihydroxyisopropylamide); and (ix) drying said washed solid L-5-α-hydroxypropionylamino-2,4,6-triiodo-isophthalic acid bis-(1,3-dihydroxyisopropylamide).

* * * * *